(12) United States Patent
Vieira

(10) Patent No.: US 8,925,905 B2
(45) Date of Patent: Jan. 6, 2015

(54) DEVICE FOR DISPENSING VOLATILE SUBSTANCES, IN PARTICULAR FRAGRANCES AND/OR INSECTICIDES

(75) Inventor: Pedro Queiroz Vieira, Cascais (PT)

(73) Assignee: CTR, LDA, Samora Correia (PT)

( * ) Notice: Subject to any disclaimer, the term of this patent is extended or adjusted under 35 U.S.C. 154(b) by 455 days.

(21) Appl. No.: 13/390,794

(22) PCT Filed: Aug. 19, 2009

(86) PCT No.: PCT/EP2009/006011
§ 371 (c)(1),
(2), (4) Date: Aug. 2, 2012

(87) PCT Pub. No.: WO2011/020480
PCT Pub. Date: Feb. 24, 2011

(65) Prior Publication Data
US 2012/0298774 A1 Nov. 29, 2012

(51) Int. Cl.
*B01F 3/04* (2006.01)
*A61L 9/12* (2006.01)
*A01M 1/20* (2006.01)

(52) U.S. Cl.
CPC .............. *A01M 1/2033* (2013.01); *A61L 9/122* (2013.01); *Y10S 261/88* (2013.01)
USPC .......... 261/26; 261/30; 261/101; 261/DIG. 88

(58) Field of Classification Search
USPC .......... 261/26, 30, 101, DIG. 88; 239/58, 202
See application file for complete search history.

(56) References Cited

U.S. PATENT DOCUMENTS 2,629,149 A * 2/1953 Yaffe ............................ 422/124

* cited by examiner

*Primary Examiner* — Robert A Hopkins
(74) *Attorney, Agent, or Firm* — Southeast IP Group, LLC; Cort Flint; Thomas L. Moses

(57) ABSTRACT

The invention relates to a device for dispensing volatile substances, in particular fragrances and/or insecticides, comprising at least one storage medium (34, 35) that contains, in particular temporarily stores, the at least one substance to be dispensed, and at least one means (9) for producing at least one air flow, wherein the at least one air flow (47, 54) is directed toward the at least one storage medium (34, 35) in such a way that the air flow increases the rate of dispensation to the environment of the substance to be dispensed relative to the state in which a flow is not directed at the storage medium.

35 Claims, 13 Drawing Sheets

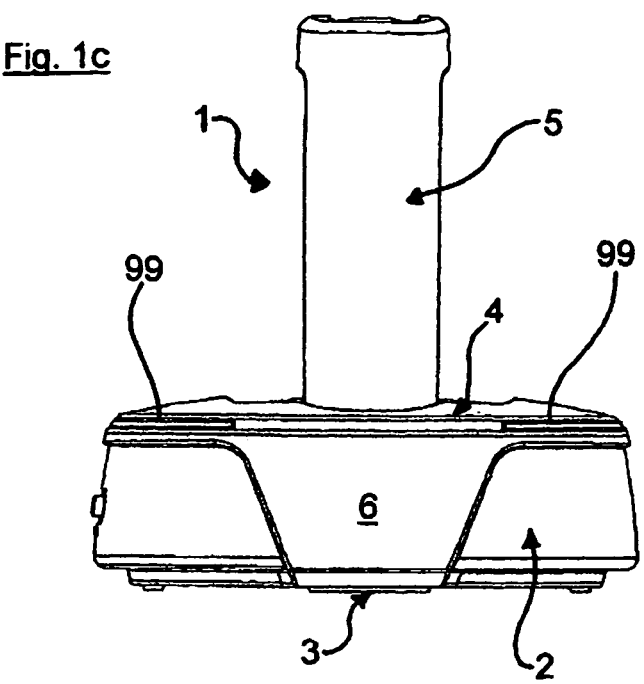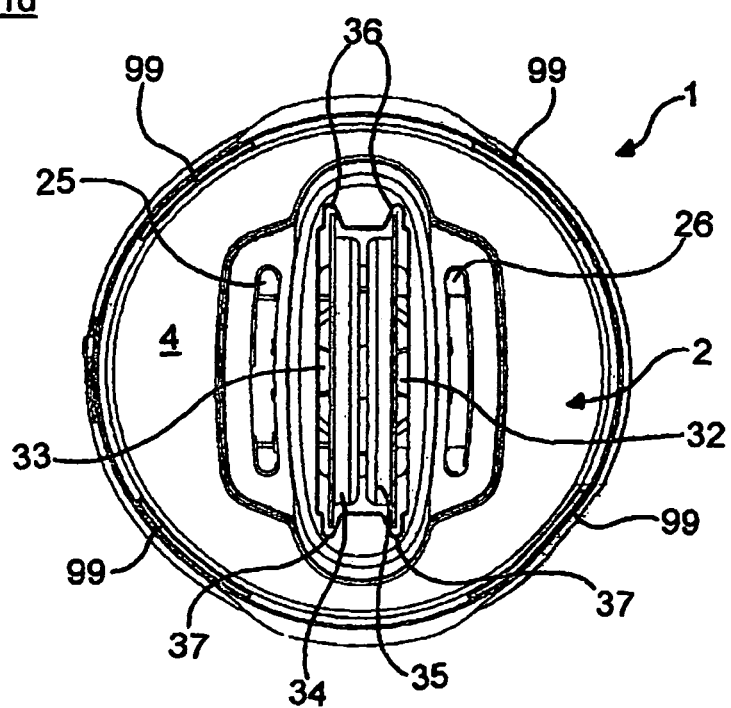

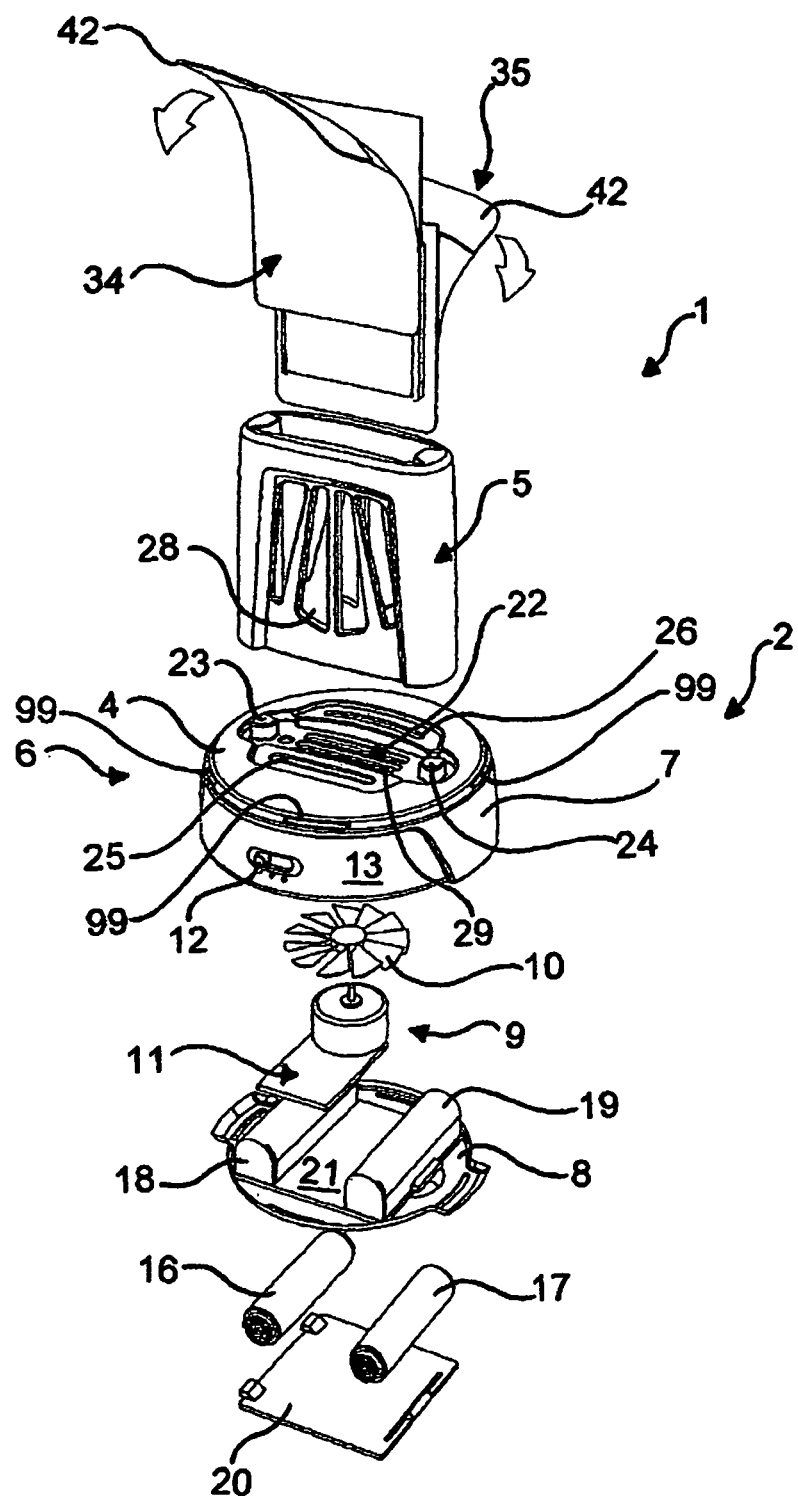

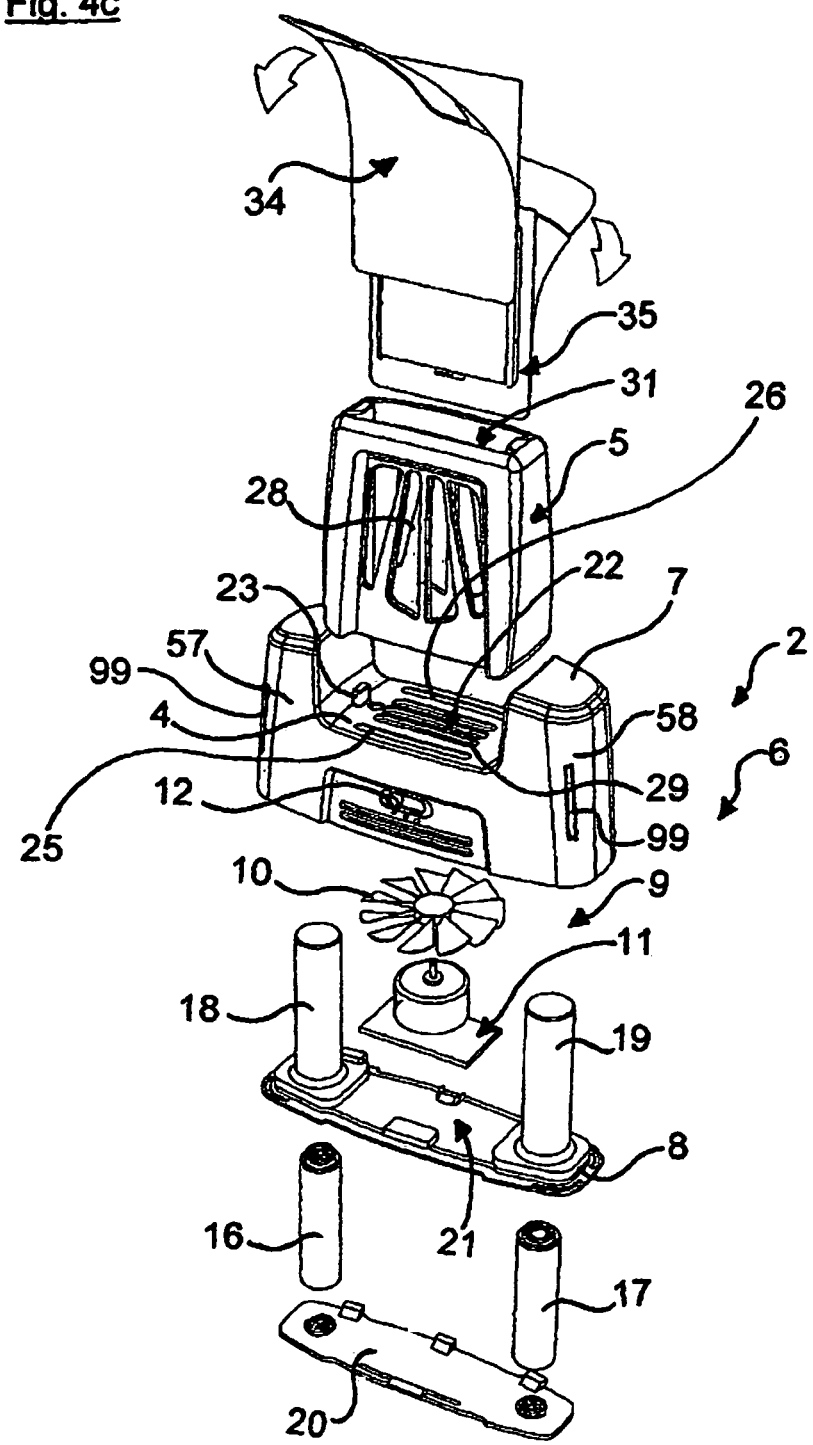

Figure 1A:
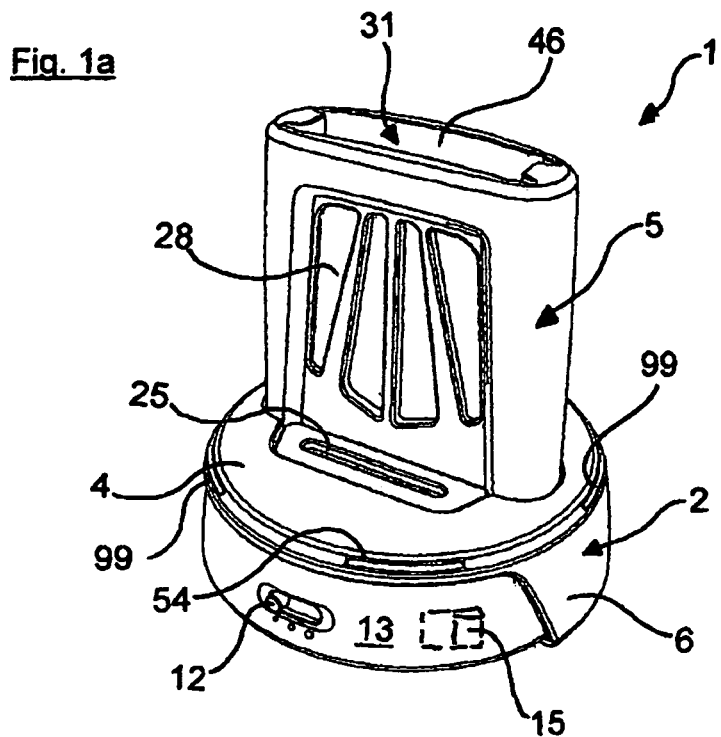
Figure 1B:
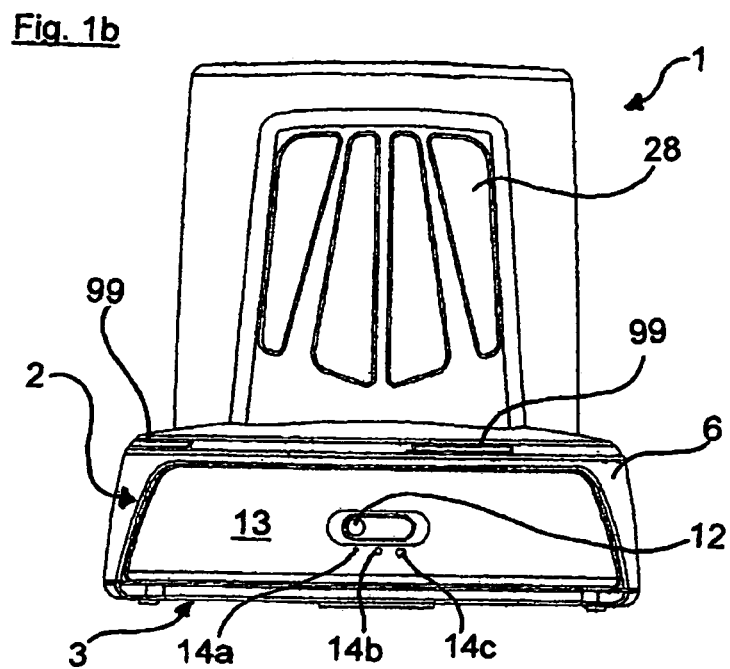

DEVICE FOR DISPENSING VOLATILE SUBSTANCES, IN PARTICULAR FRAGRANCES AND/OR INSECTICIDES

BACKGROUND OF THE INVENTION

The invention relates to a device for dispensing volatile substances, in particular fragrances and/or insecticides.

Such devices for dispensing volatile substances are generally known, for example, in combination with a vaporization device having a heating device, a wick saturated with liquid protrudes into a recess of the heating device for increasing the evaporation rate.

In contrast, it is the object of the present invention to provide an alternative device for dispensing volatile substances, in particular fragrances and/or insecticides, by effectively dispensing agents or substances to the environment in a structurally simple, functionally reliable and user-friendly construction without a heating device.

SUMMARY OF THE INVENTION

This object is achieved, according to the invention, by providing a device for dispensing volatile substances having a temporary storage medium which stores a substance to be dispensed and a means for producing an air flow. The air flow is directed toward the storage medium in such a way that the airflow increases the rate of dispensation of the substance into the environment compared to the state in which a flow is not directed toward the storage medium.

Preferably it is provided, that the produced air flow is directed around and/or at the storage medium in a defined region.

Using such a solution according to the invention, an increase in the rate of dispensation or "evaporation rate" of the stored substance is achieved wherein at least one liquid and/or gel diffuses into the environment from the storage medium by means of a membrane. By directing the air flow at such storage medium by means of a defined air flow, the dispensation or the diffusion of the substance to be dispensed is accelerated by the membrane which in turn increases the product efficiency significantly.

Here, expressly, the term "substance to be dispensed" is to be understood in a broad sense and includes any agent that can be vaporized or volatilized into the environment, such as fragrances and/or insecticides.

Preferably, a means for producing the air flow is formed by a ventilator, blower, and/or fan assembly having, for example, at least one rotor, and/or propeller-like impeller. In principle, however, any other suitable means for producing the air flow can be used. Hereinafter, for reasons of clarity, the invention will be always described in combination with the term fan assembly as the illustrated means for producing the airflow. It being understood that the term is not intended to be limited to the illustrated fan assembly. Rather, the terminology fan assembly is to be understood in a broad sense.

According to a preferred embodiment of the present invention, the fan assembly is part of a docking station by means of which the at least one storage medium is retained in, and/or can be detachably connected at the docking station. The storage medium may be retained by means of a component retaining, and/or receiving the storage medium, hereinafter described in more detail.

The docking station has a function comparable to a charger, for example, for electrical appliances, such as telephones or the like, on which the respective storage medium is docked in the simplest manner. Preferably, it is provided in combination with a set, or several different retaining means described hereinafter in more detail. The retaining and/or receiving means for the storage medium can be docked user-specifically, and/or according to the desired specific application for use to a single docking station. For example, the retaining or receiving means can differ in terms of shape, and/or pattern of air inlet openings. Similarly, the retaining or receiving means can differ also in terms of the number and the manner of storing the storage therein.

It is particularly advantageous if the docking station has a single, or multi-part housing in which the fan assembly is received. On the one hand, this provides a contact protection and on the other, a defined air stream can be set by means of, for example, defined air outlet and inlet opening geometries. This means that the housing has at least one air outlet opening enabling this air discharge.

In principle, the air outlet opening can also function as an air inlet opening. However, for a good operability it is particularly advantageous to provide the air inlet opening at a suitable position on the housing separately and independently from the air outlet opening. This is particularly advantageous if the fan assembly, in particular its impeller, is associated directly to the air outlet opening. For example, the impeller is arranged in the housing in conjunction with a housing top comprising the air outlet opening, directly below the same, while the air inlet opening is preferably arranged spaced therefrom in the more lateral region of the housing. For example, the air inlet opening is arranged at a side wall and/or at the transition region between a side wall and a housing top. This ensures that the air flow produced by the fan assembly is directed preferably more or less directly at the air outlet opening, by which in turn, the desired flow conditions can be set in a simple and reliable manner. In principle, an indirect air feeding from the fan assembly to the air outlet opening is also conceivable, for example, by means of a flow channel or the like.

Particularly preferred is an embodiment wherein the docking station is formed as a free-standing appliance comprising a connection area for the storage medium, or for a component optionally retaining or receiving the same. The appliance may be placed on a surface, such as a table, on the ground, or on a shelf. Preferably, the connection area is formed by an upward-facing upper surface of the docking station from which the docked storage medium, or the component receiving the storage medium, projects upward in a defined spatial direction, preferably in a high vertical direction, in a tower-like, or in a block-like manner.

Such a device for dispensing volatile substances designed as a docking station results in a completely novel concept of an "evaporation" device, which can be individually equipped and used with very reliable and user-friendly functions. An operator immediately and readily recognizes the technical functioning of such a design principle, which he/she knows, for example, from chargers for electronic components, which in turn leads to high customer acceptance.

To ensure that a sufficient amount of air flow can flow to the storage medium, according to another particularly preferred embodiment, it is provided that the housing of the docking station on a side of the housing facing the storage medium has one air outlet opening, in particular an air outlet slot as air outlet opening. In particular in conjunction with such an embodiment, it is advantageous that the air outlet opening, and/or the fan assembly, and/or the storage medium are arranged and/or are associated to one another in such a way that the air flow flows to a defined extent toward and/or around the storage medium. Particularly preferred is a specific embodiment in which the air flow flows toward and/or around the storage medium along a defined air flow area of the storage medium. Such a defined air flow area can be formed, for example, at the previously described membrane region.

As already indicated several times, according to a particularly preferred embodiment of the present invention idea, it is provided that the at least one storage medium is received or retained in a retaining and/or receiving means which can be connected, in particular detachably connected with the docking station in a docking region, preferably can be placed thereon and/or docked thereto from above. Here, expressly, the terminology retaining and/or receiving means is to be understood in a broad sense and shall include any means of retaining of the storage medium and not just, albeit preferred, the reception of the storage medium in a receiving space and thus in the interior of the retaining and/or receiving means.

Utilizing such a retaining and/or receiving means yields the previously described advantages, particularly with regard to a functionally reliable positioning and retaining of the respective storage media in the device or in the appliance in conjunction with different design options to satisfy very different design requirements. Of course, by employing such retaining and/or receiving means, for example, by the manner the air outlet opening is configured, the air stream directed toward the storage medium can be affected, for example, in terms of the quantity and the volume or also in terms of air velocity. Thus, this results in most individual design options of such devices according to the invention.

In particular, having such retaining and/or receiving means the new technical concept of a docking station takes effect, for example, by inserting in a first step the storage medium into the retaining and/or receiving means and subsequently preferably docking the retaining and/or receiving means equipped in such a manner above the docking station. Insertion of the storage medium likewise takes place preferably from above, i.e., at an end of the retaining and/or receiving means, facing away from the docking section in which the storage medium is inserted, preferably from above. It is to be understood that the storage medium can be inserted into the retaining and/or receiving means even after docking of the retaining and/or receiving means to the docking station.

Advantageously, the detachable connection of the docking station with the retaining and/or receiving means takes place by means of a mechanical latching, and/or support, and/or plug-in connection, wherein a form-fitting and/or friction-fitting connection is preferred. According to a specific embodiment, for example, a docking station-side latching, and/or support, and/or plug-in member is arranged at the docking station. In the docked connected state of retaining and/or receiving means and docking station the member(s) cooperate with a retaining and/or receiving means-side latching, and/or support, and/or plug-in member in such a way that the retaining and/or receiving means is held by a defined retaining force in and/or at the docking station or the docking region. This can be done specifically, for example, on the one hand by latching lugs or latching pins that are associated to one another, and latching recesses on the other.

Specifically, the retaining and/or receiving means has at a defined region of an outer wall an air inlet opening through which an air flow, delivered out of the docking station-side air outlet opening, can flow into and/or optionally out of the same from outside of the retaining and/or receiving means. Thus, such air inlet openings form preferably side air inlet openings advantageous with structures formed from storage medium and retaining and/or receiving means in which a membrane region is arranged in the immediate vicinity of the side air inlet openings provided, i.e., facing it. This allows the efficient dispensation of substances, and thus enrichment of the respective substances to be dispensed in the flowing air.

Particularly preferred, the side air inlet openings form a defined opening pattern that releases at least 20%, and most preferably at least 40% of the associated storage medium area in order to achieve adequate and technically reasonable flow conditions.

A particularly effective enrichment of the airstream with the dispensed substances takes place when several dock air outlet openings, preferably spaced from one another, are formed by air outlet slots arranged at the docking station in the docking region around the retaining and/or receiving means and are assigned to retaining and/or receiving means wall regions. The wall regions have the retaining and/or receiving-side air inlet openings. The association is made here in particular in such a way that air flows exiting from the docking air outlet openings are on a defined, substantially straight flow path to the air inlet openings.

According to a particularly preferred specific embodiment variant, the retaining and/or receiving means has a block or box-like outer contour comprising the air inlet openings on opposing outer wall sides. In addition, in the docking region, on opposing sides of the retaining and/or receiving means associated with the wall sides comprising the air inlet openings, at least one docking station side air outlet opening is formed by an air outlet slot. This results in a more compact device structure, enabling an easy and effective enrichment of the ambient air.

According to a further variant of the invention, the docking station may have a U-shaped outer contour with U-legs which encompass at least partially form-fittingly the retaining and/or receiving means. In particular, the legs encompass at least partially form-fittingly at the opposing outer wall sides facing away from the air inlet and air outlet openings associated to one other. This achieves an even better support and retention of the retaining and/or receiving means at the docking station.

Advantageously, it may be provided that the air inlet opening of the retaining and/or receiving means is formed so that the air flow flows around the storage medium from below along a defined path, and/or that it is flow-connected with at least one retaining and/or receiving means side flow channel, by means of which the air flow is led to the receiving space. In principle, this variant of the invention may be provided as an alternative to the above described lateral air inlet openings of the retaining and/or receiving means which are associated to the exposed air outlet openings of the docking station. Particularly, this variant of the invention is provided in addition to the lateral air inlet opening formed at the retaining and/or receiving means side to which the exposed, docking station side air outlet opening is associated with the retaining and/or receiving means. With this design a particularly effective substance enrichment of the flowing air can be achieved. This ensures, for example, in conjunction with a membrane region of a storage medium, that a high volume of air flows over or along this membrane region and a very high substance dispensation or substance diffusion in the environment is effected.

In order to flow out of the retaining and/or receiving means, a discharge opening is provided thereon. It may be formed, for example, by an access opening of the receiving space, through which the storage medium can be inserted into the receiving space. Alternatively or additionally, the discharge opening can be formed in a dual function, but also by the side air inlet opening enabling the entrance of the air flow into the receiving space.

The membrane region of the storage medium, by means of which the substance to be volatilized is dispensed toward and/or around the membrane region. The air flow, may be formed in different ways or by different materials, for example, by a diffusion film. Fiber materials or textiles can also be used.

A preferred structure of the storage medium, which is claimed expressly independently from any and all previously described features of the invention, provides that the storage medium is formed by a container in which the substance to be dispensed or to be volatilized, for example, in form a liquid and/or a gel, is received, wherein a defined container wall region is designed as a membrane region. Preferably, this membrane region is covered and/or sealed by a removable covering, for example, a peel-off film or the like. This peel-off film can be formed, for example, from an aluminum material or the like. This covering is removed immediately prior to inserting the storage medium into the device, such that dispensation of substance to the extent desired takes place in the device itself and not earlier, when the storage medium is not yet in use.

Preferably, the storage medium has a plate-like and/or rectangular shape, and a membrane region of the storage medium is formed at least partially by at least one of the two large lateral areas. Thus, a large area is provided, by means of which the substance can diffuse out of the container into the environment. In addition, a large contact area for the flow of air is provided which increases the effectiveness of the enrichment of the ambient air with the desired substance.

Preferably, such plate-like and/or rectangular storage medium is inserted into the retaining and/or receiving means by means of a side access opening, preferably guided and inserted, and/or positioned by means of a kind of guiding means. In a particularly preferred embodiment, the retaining and/or receiving space comprises at least one insertion slot with guide grooves spaced on opposing sides in which the plate-like and/or rectangular storage medium engages the edge-side opposing edge plate regions and can be transferred into the given storage medium position, and/or can be supported and/or retained therein in a guided manner. Such an embodiment of the receiving space of the retaining and/or receiving means comprising at least one insertion slot, results in a very simple and functionally reliable operation by the operator when inserting or replacing or replenishing a storage medium.

In principle, the retaining and/or receiving means, or its receiving space, can be designed in such a way that only a single storage medium can be inserted into it. Preferred, however, is a receiving space, in which several, in particular two insertion slots are provided, that are substantially identically designed and spaced from one another transversely to the insertion direction. In this manner, identical or different substances can be volatilized, for example, two with each having harmonizing fragrances, or a fragrance and an insecticide, or two insecticides, to name a few. Of course, with such a design the use of only a single storage medium is possible. In this case, the remaining insertion slots are not equipped with storage media.

For a functionally reliable positioning, it is further advantageous if the storage medium inserted into the insertion slot is supported in the insertion position by means of a retaining side and/or docking station side stop member. For this purpose, for example, corresponding stop projections are provided in the receiving space of the retaining and/or receiving means, for example, at the insertion slot end opposing the insertion opening.

The means for producing the air flow, which is preferably formed by a fan assembly, is preferably actuated electrically, and preferably by means of an energy storage device such as a battery or a rechargeable battery. Alternatively, the energy supply can also be provided by means of an electric power grid. In the latter case, a cord extends from the device, for example from the docking station, which can be connected by means of an outlet. Optionally, the plug-in unit can be mounted directly onto the device, for example, onto the docking station such that in this case a cable may be omitted. To accommodate the energy storage device, the device preferably comprises a receiving compartment for batteries which can be latched by a cover member such as a flap or by lid. This cover member can either be designed pivotally hinged, or completely detachably.

For a particularly compact design in case of a plurality of energy storage devices or in case of energy storage devices received in receiving compartments, the receiving compartments form a mounting space in which the fan assembly, optionally together with other components of the device, is mounted. The other components can be, for example, other electrical components, such as a printed circuit board, a chip, or a lighting device and the like.

In conjunction with the energy storage device it may be provided that the energy storage device is aligned horizontally and/or vertically in the interior of the docking station, based on the operating position of the device. A substantially horizontal alignment of the energy storage devices results in an overall flatter, more disc-like design of the docking station. The retaining and/or receiving means for the storage medium may be placed on a contact area, projecting upward as in a tower from the docking station.

In the case of vertically arranged energy storage devices and receiving compartments, a fork-like or U-shaped receptacle can be formed at the housing of the docking station. The receptacle encompasses or supports the storage medium in a form fittingly or contact connection.

In principle, there is the possibility that the vaporization device appliance according to the invention provides only a single operation or mode of operation. For example, in case of an activated device, a certain amount of air is produced by the fan assembly and this air flows, for example, through the docking station side air outlet openings to the side receiving means side air inlet openings. The amount of air, the air velocity, or the influx and discharge cross-section of the air inlet and air outlet openings can be changed. Alternatively, however, a control or regulating means can be provided for controlling the fan assembly as a function of defined operating parameters such as adjusting the velocity or the amount of the air flow delivered to the storage medium. For example, by means of the control or regulating means the fan assembly can be controlled so that the speed of a fan wheel is decreased or increased in order to perform the corresponding adjustment of the air quantity or to adjust for the presently selected mode of operation. Alternatively or, additionally, the closure member can be provided, for example, a flap or the like, by means of which the opening cross-section of the air outlet opening is blocked or opened as a function of predetermined operating parameters. The closure member may, for example, be designed manually adjustable. In principle, the control or regulating means has a control option as a function of defined operating parameters, such as the velocity or the amount of air flow, wherein the adjustment is effected preferably by means of corresponding actuators.

According to another preferred embodiment, the control or regulating means comprises a memory in which pre-programmed modes of operation or operating cycles are stored. Thus, depending on user requirements, different programs can be run and, for example, different substance dispensation quantities can be set. For example, set depending on time of day or the season, and/or the application.

Advantageously, the fan assembly is deactivated and the substance to be evaporated and dispensed from the storage medium without air flow by the fan assembly. Further, at least one additional mode of operation is provided in which the fan assembly can be activated for a defined period of time and an air flow supporting the dispensation of the substance can be produced. In conjunction with this an additional mode of operation, again different programming or processing may be provided such as a mode of operation in which the fan assembly is permanently activated. Alternatively, at least one additional mode of operation may be provided in which the fan assembly is activated for a defined period of time and subsequently is deactivated for a defined period of time. Preferably, the individual activation and deactivation phases repeat periodically or cyclically. In case of several additional modes of operation it is provided that these modes of operation differ with respect to activation and deactivation operations, in particular the speed of the fan assembly. For selecting the different modes of operation a single switch member may be provided by means of which, in a first switch position, the fan assembly is not actuated. However, in a second switch position, the fan assembly is activated for a defined period of time, such as 15 minutes, and is deactivated for a further, subsequent period of time such as, again, 15 minutes. These activation and deactivation phases repeat in a program controlled manner until the switch member is moved into another position. For example, a further switch member position may be provided in which the fan assembly is actuated in an exemplary fashion for a longer period of time, such as 30 minutes, and then a shorter deactivation phase is selected, such as 15 minutes. A further switch member position may also be provided in which the fan assembly is permanently in operation. Regardless of the possibility to be able to set the intensity of the substance dispensation into the environment, here the additional advantage in particular is that the battery life can be conserved by providing selection and operation options in which the fan assembly is not actuated permanently.

From a general perspective, according to a preferred embodiment, it is provided that the device has a switch member, that is preferably accessible from the outside, by means of which the respective desired operating state can be selected, and the fan assembly can be actuated and can be switched on or off. Several switches may be provided such as a first switch to switch the device on or off and a second switch to select the respective desired state of operation. For example, it may be provided that the modes of operation do not include any mode of operation wherein the fan assembly is switched off, since this operating state already has been achieved by the switching off effected by the first switch. In principle, however, a single switch may be provided, by means of which the device can be switched both on or off, and also the respectively desired operating state and mode of operation can be selected, as explained above.

Further, a light emitting means such as a light emitting diode and the like may be provided for displaying the respective operating state and mode of operation. The docking station and the storage medium and the component receiving the storage medium can be illuminated. This is particularly advantageous when the retaining or receiving means which is receiving the storage medium, is formed at least partially from a transparent material, for example, from a glass and/or plastic material. A certain light effect can be produced in certain defined regions of the retaining or receiving means. Particularly in the latter case the light emitting means in the docked state is covered by the retaining or receiving means.

According to a particularly advantageous solution according to the invention, the device is formed as a set having several different retaining means which are compatible with the docking station. In this way, only a single docking station is part of this set, which then can be equipped or formed individually with different retaining or receiving means. Of course, also the storage medium can be a set component.

DESCRIPTION OF THE DRAWINGS

The invention will be more readily understood from a reading of the following specification and by reference to the accompanying drawings forming a part thereof, wherein an example of the invention is shown and wherein:

FIGS. 1*a* through 1*m* show schematically different views of a first embodiment of the present invention;

FIG. 2 shows schematically a second embodiment of the present invention;

FIG. 3 shows schematically a third embodiment of the present invention;

FIGS. 4*a* through 4*g* show schematically different view of a fourth embodiment of the present invention;

FIGS. 5*a* and 5*b* show schematically a preferred embodiment of a storage medium of the invention; and FIGS. 6*a* through 6*c* show different detailed views of a receiving means of the invention.

DESCRIPTION OF A PREFERRED EMBODIMENT

FIG. 1 shows different views of a first exemplary embodiment of the invention. FIG. 1*a* shows a schematic, perspective front view, FIG. 1*b* shows a front view, FIG. 1*c* shows a side view and FIG. 1*d* shows a plan view of a device 1 in the assembled state. Device 1 comprises a docking station 2 designed as a free-standing appliance with a station contact area 3 and a connecting area 4 for a retaining or receiving means simply denoted as receiving means 5.

The docking station 2 is formed, as illustrated, by a housing 6 having an approximately circular disc geometry, which, as can be seen from the perspective view in FIG. 1*e* is formed by a housing top 7 and a housing bottom 8.

Housing top 7 and housing bottom 8 can be connected with each other detachably, for example, by a clip or latching connection (which is not illustrated in detail) and be formed correspondingly at an edge side at the housing top 7 and at the housing bottom 8. In the interior of housing 6, as can best be seen in FIG. 1*e*, an electrically actuatable fan assembly 9 is arranged comprising an impeller 10 to generate an air flow in a manner to be described in more detail. Fan assembly 9 is coupled to a control regulating means 11, which is illustrated without and schematically represented by a circuit board. By means of a position of a manual switch 12 (see FIGS. 1*a*, 1*b*), in a side wall portion 13 of housing 6, a certain mode of operation can be selected. In the exemplary case shown three different modes of operation or operating states can be selected, which are characterized by different markings 14*a*, 14*b* and 14*c* (FIG. 1*b*). In a switch positioning in the region of marking 14*a*, the fan assembly 9, for example, is turned off. In a position at marking 14*b* of the manual switch, the fan assembly 9 can be activated, for example, with a defined speed for a defined time, for example, 15 minutes. Subsequently, the fan assembly 9 can be deactivated for a defined period, for example, also 15 minutes. After this deactivation phase, the fan assembly 9 is then activated again and the cycle begins anew. In a manual switch position in the region of the marking 14*c*, the mode of operation then changes again and, if, for example, the duration of the activation and deactivation phases is changed from the switch position 14b, the respective activation phase is longer, for example, 30 minutes, while the deactivation phase remains the same, in the exemplary case at 15 minutes. In principle, in switch position 14c it could be provided that fan assembly 9 is activated permanently. This could optionally also be realized with an additional switch position, not shown here. The previous explanations are intended to illustrate the variation possibilities in an exemplary fashion only, and of for limitation.

As is illustrated in FIG. 1a, schematically and with dashed lines, an additional, separate manual switch 15 may be provided for switching device 1 on or off, so that manual switch 15 is used only to select the respective mode of operation.

As can best be seen from FIG. 1e and FIGS. 1j to 1m, batteries 16, 17 are provided for the electrical actuation of fan assembly 9. The batteries may be inserted in housing bottom 8 via receiving compartments 18, 19 which are accessible via contact area 3 of docking station 2. For this purpose, at contact area 3 of housing bottom 8 and thus of housing 6, a removable and detachably latchable lid 20 is provided, which, in a removed state, reveals the receiving compartments 18, 19. FIGS. 1j to 1m show how lid 20 can be removed, and batteries 16, 17 can be removed from receiving compartments 18, 19.

As is particularly apparent from FIG. 1e, receiving compartments 18, 19 stick out from the top of housing bottom 8 and form horizontally oriented, projection-like elevations on opposing sides of housing bottom 8, which form a mounting space 21 in between. In space 21 the fan assembly 9, optionally together with further electronic components of a control or regulating means 11 are received. This results in an overall flat and compact design of housing 6.

As already described above, for receiving means 5 housing top 7 has a connector area 4 for docking in a docking region 22. In docking region 22, as is particularly apparent from FIG. 1e, two spaced latching projections 23, 24 are provided. The latching projections are arranged on opposing sides to form latching members. As is particularly apparent from FIG. 6a, the latching members engage in receiving means 5 in such a way that the receiving means is retained or supported detachably at docking station 2 with a predetermined retaining force.

Figure 1F:
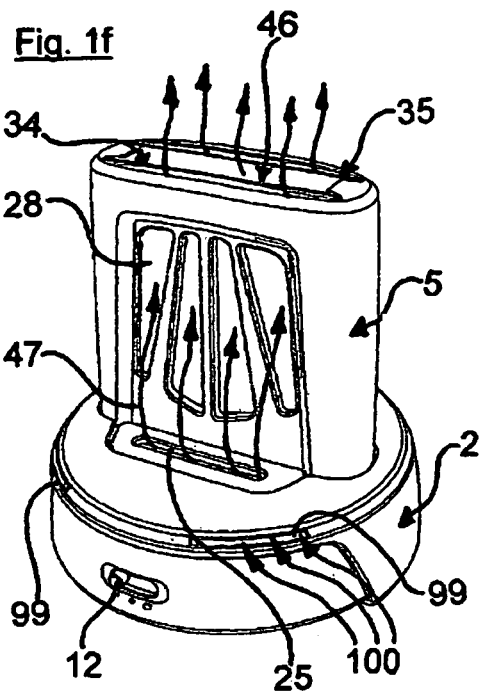
Figure 1G:
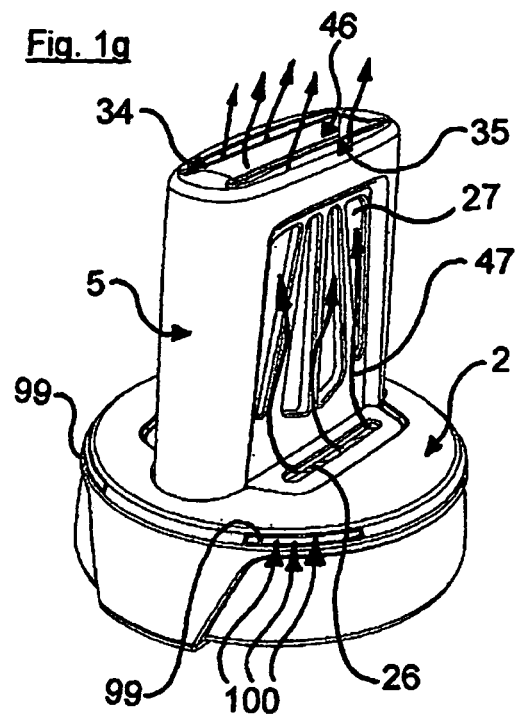
Figure 1H:
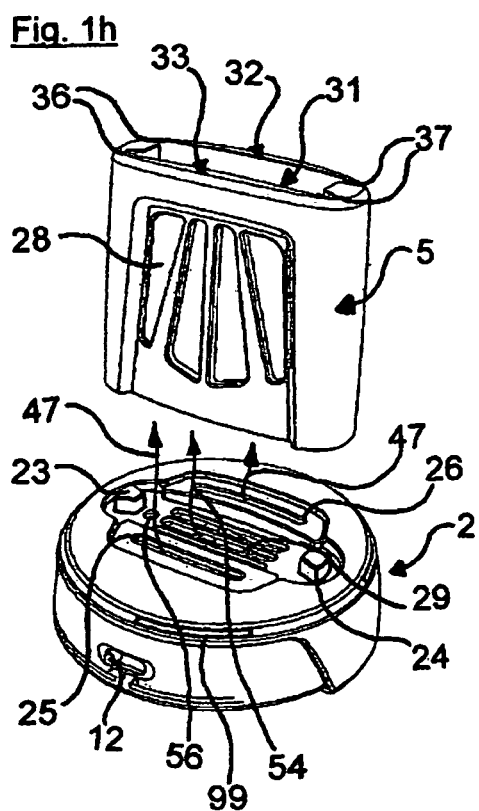
Figure 1I:
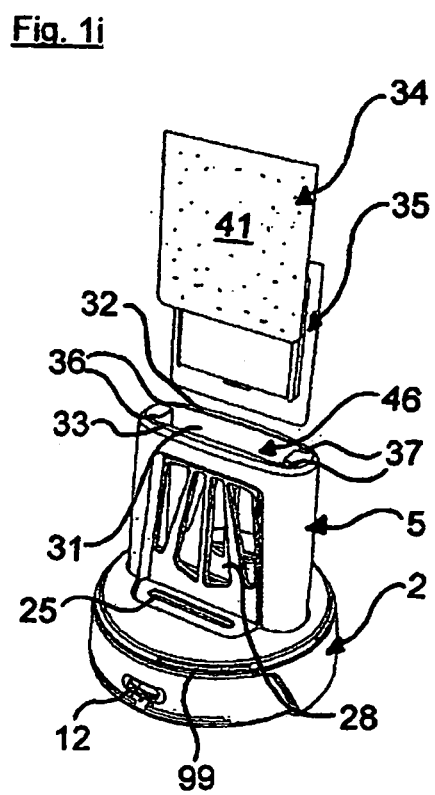
Figure 1J:
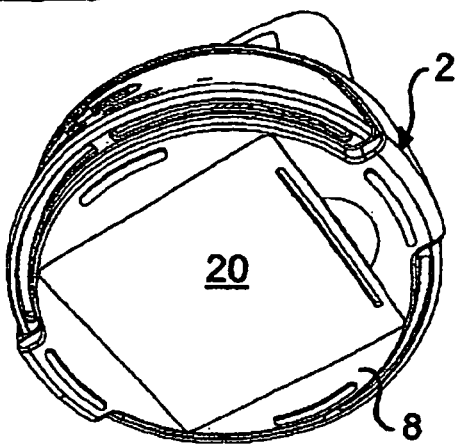
Figure 1K:
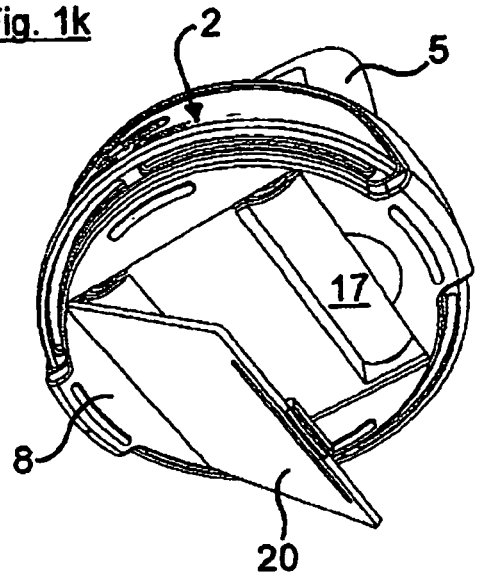
Figure 1L:
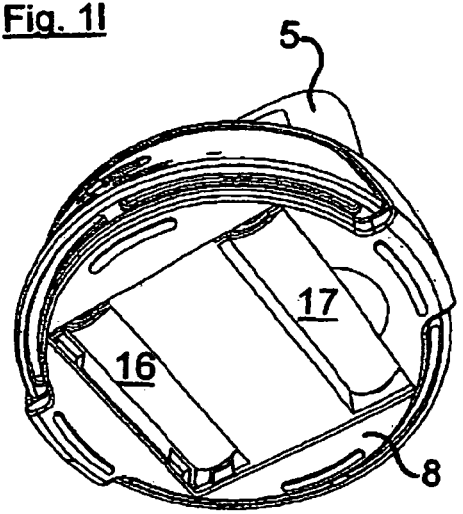
Figure 1M:
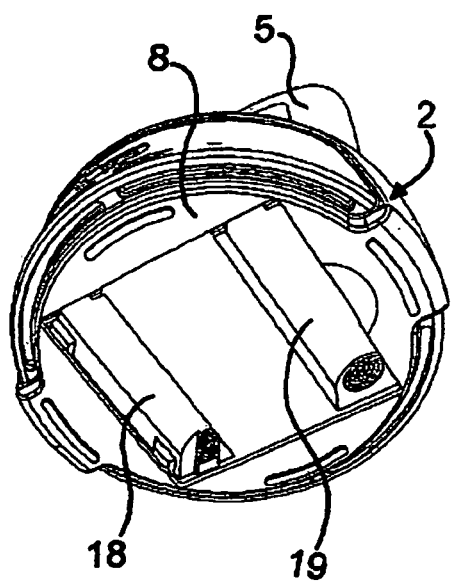

In the docked state of receiving means 5, as shown for example in FIGS. 1f, 1g, and 1i, on each of the opposing long sides of receiving means 5 there are air outlet opening slots 25, 26 of the docking station to which lateral air inlet slots 27, 28 of the receivers are associated.

Here, as well as in the following exemplary embodiments, the number and shape of the air inlet and air outlet openings are selected only in an illustrative fashion. Of course, other shapes with respect to slot geometry, for example, or a different number of openings or slots are conceivable.

Furthermore, it is provided in the region between the two exposed air outlet slots 25, 26 (i.e., in the region between the two opposing latching projections 23, 24), three additional internal air outlet slots 29 of the docking station are arranged enclosed by receiving means 5.

Furthermore, air inlet slots 99 are provided in housing 6, by means of which (as is particularly apparent from FIG. 1f and FIG. 1e), ambient air 100 is drawn into the housing interior. As illustrated, air inlet slots 99 are spaced from one another in an upper corner region of housing 6. In principle, however, the slots can be arranged at other locations, such as in sidewall region 13 of the housing top 7.

Fan assembly 9, together with fan wheel 10, is received and arranged in housing 6 in such a way that air flow 47 is directed directly toward air outlet opening slots 25, 26 or 29.

The receiving means further has a receiving space 31 with two insertion slots 32, 33 (FIG. 1). A plate-like and/or rectangular substance container 34, 35 can be inserted into slots 32, 33 as a storage medium for the substance to be volatilized.

Insertion slots 32, 33 are spaced from one another transverse to the insertion direction and each has opposing guide grooves 36, 37, in which the plate-like and rectangular substance container with edge-side opposing edge plate regions 38, 39 engages and are guided to the end position (FIG. 1d).

Figure 5B:
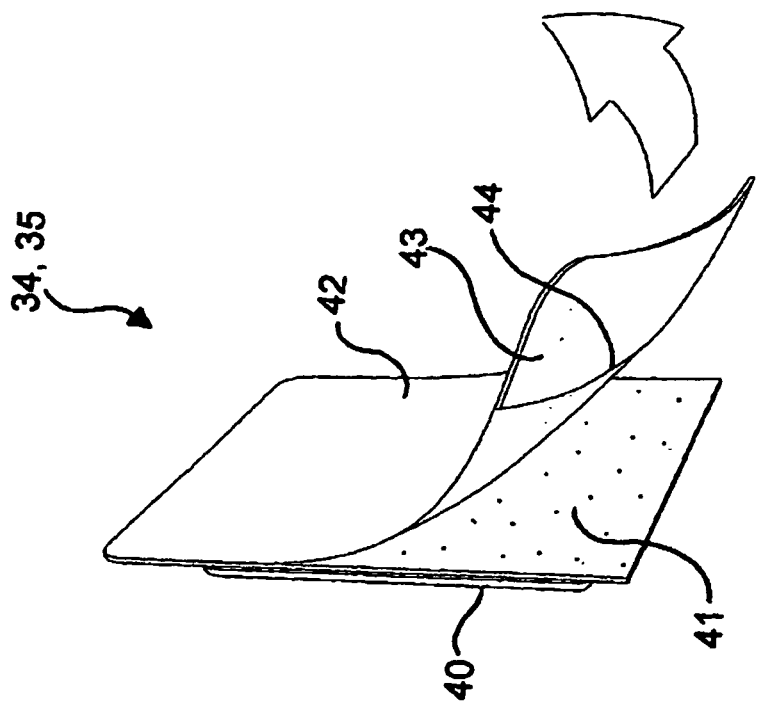
Figure 5A:
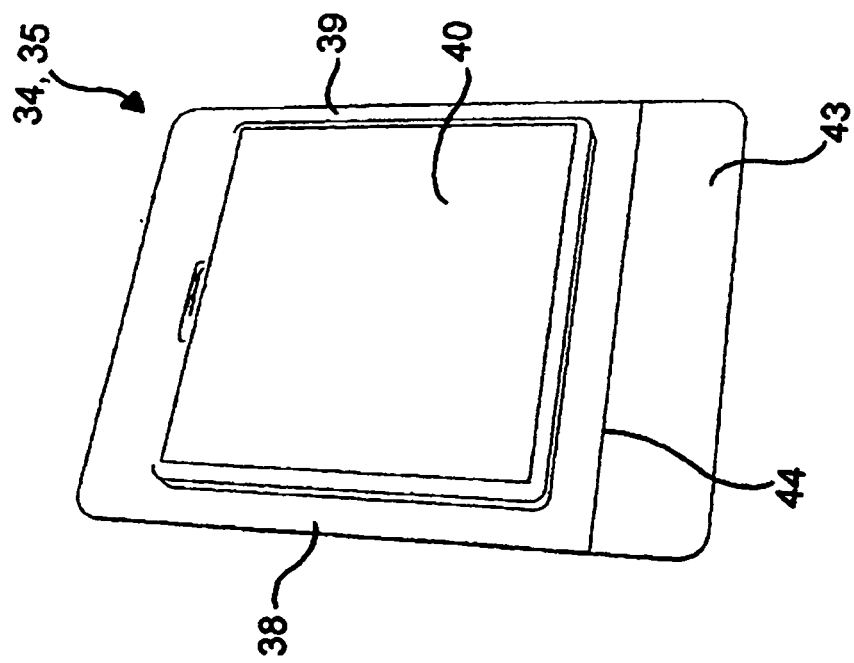

As is apparent from FIG. 5a, the substance container has a tub-shaped receptacle 40 for the substance to be volatilized which may be formed, for example, by a liquid or a gel. As is apparent from FIG. 5a, this tub-shaped receptacle has a flat, cuboid-like outer contour. The tub-shaped receptacle 40 is covered by a membrane film 41 which is provided with a dot pattern (FIG. 5b). By means of this membrane film 41, the liquid received in the tub-shaped receptacle 40 or the gel received therein can diffuse out into the environment. For this to happen only when the container 34 or 35 is inserted in receiving means 5, membrane film 41 is sealed by a cover film 42 (FIG. 5b and FIG. 1e) which is removed immediately preceding the insertion of containers 34, 35 by a tab 43, optionally bent along a bend region 44 and subsequently peeled off membrane film 41.

In use, containers 34, 35 are inserted into assigned insertion slots 32, 33 in such a way that membrane film 41 is facing lateral air inlet slots 27, 28. If now device 1 is actuated and fan assembly 9 is powered on, ambient air 100 is drawn into air inlet slots 99, and housing 6 of docking station 2. An air flow 47 is produced (FIGS. 1f and 1g) through exposed housing air outlet slots 25, 26 and flows by means of receiver air inlet slots 27, 28 into receiving space 31 of receiving means 5. There, air flow 47 flows along the surface of membrane film 41 of containers 34, 35 upwardly. Air flow 47 is enriched by the substance diffusing through membrane film 41. The air flow, enriched with the substance to be dispensed flows (FIGS. 1f and 1g) by means of an access opening 46 of receiving space 31 into the environment.

Due to air flow 47 delivered over membrane film 41, the dispensation rate and/or quantity of the substance into the environment is increased. The effectiveness of the device with respect to a dispensation of an agent can be increased significantly. Due to the possible variation of the speed, the selection of different modes of operations or operating cycles, the velocity of the air flow, and/or the amount of air flow, the diffusion rate of the substance through the membrane film 41 can be affected.

Internal air outlet slots 29 may be provided optionally. In case they are provided, as illustrated, another air flow 54 can flow into receiving space 31 of receiving means 5. Thus an additional air supply to respective membrane films 41 of containers 34, 35 may be achieved. To enable this air supply, receiving means 5 comprises, for example (FIG. 6b), side air inlet slots 48, 49 at the bottom.

Figure 6A:
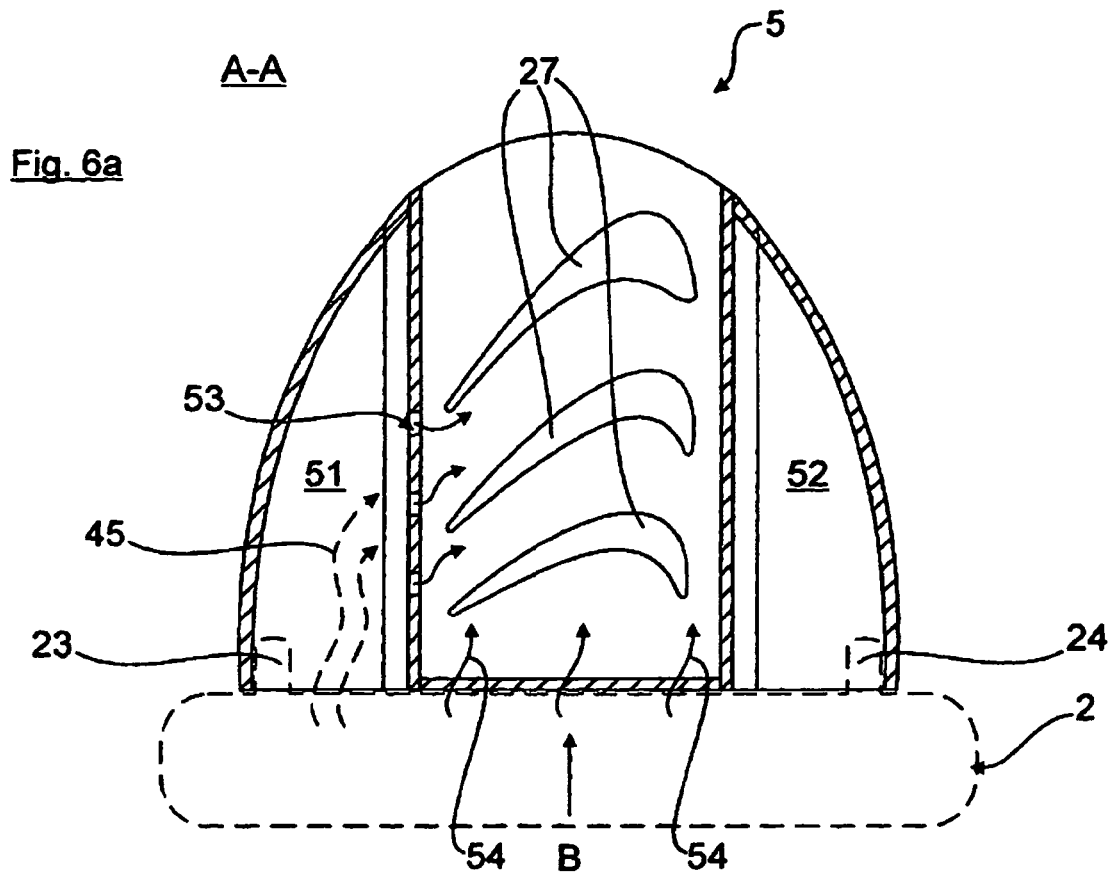
Figure 6B:
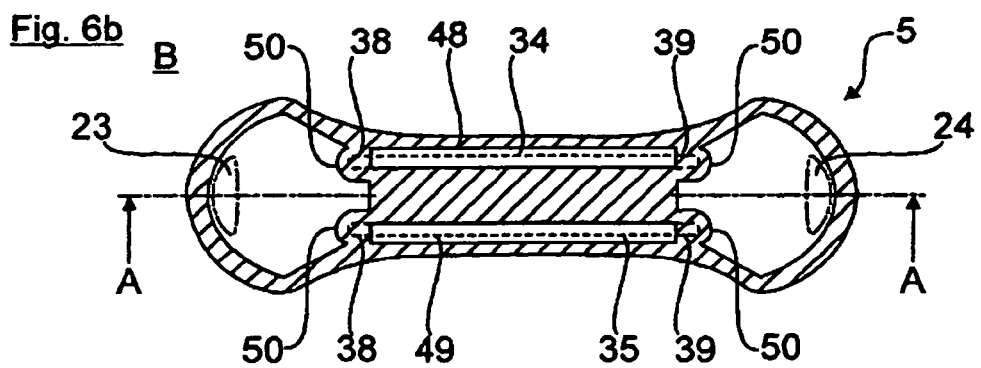

In FIG. 6b it is furthermore illustrated that two air inlet slots 48, 49 have such a longitudinal extension that stops 50 are formed at the opposing slot ends. Containers 34, 35 are supported at the stops with their respective edge plate regions 38, 39 in the inserted position. For reasons of clarity, containers 34, 35 are only represented by dashed lines.

As best illustrated in FIG. 6a, schematically and in dashed lines, internal air outlet slots 29, 30 provided in docking region 22 can have such a length that they flow into flow channels 51, 52 located on opposing sides of the receiving means 5. From there, they flow by means of at least one internal, lateral flow-through opening 53 into the region of containers 34, 35. In particular, they flow into the region of membrane films 41. This is indicated in FIG. 6a only on the left part of the drawing, in conjunction with an air flow 45.

Figure 6C:
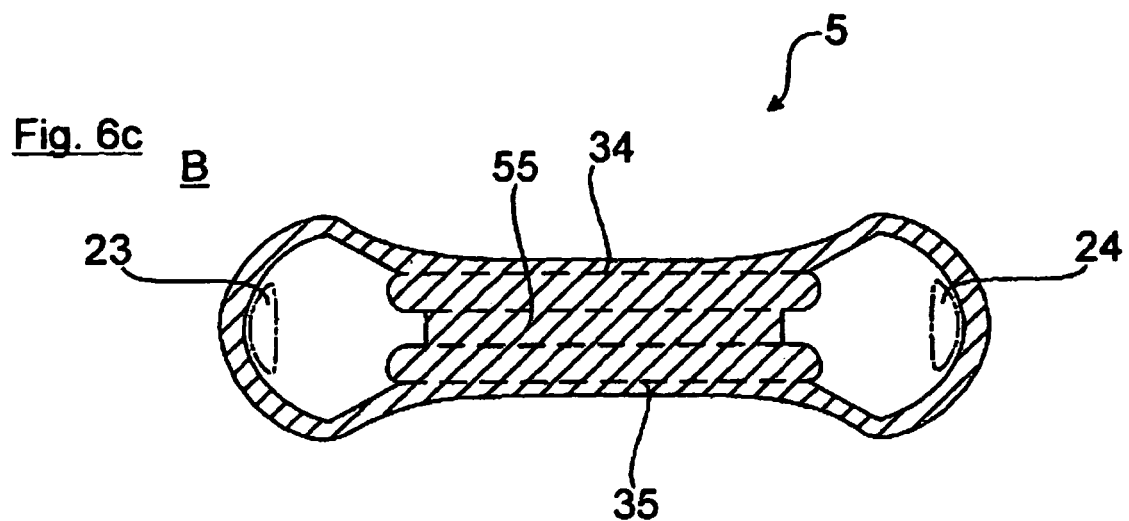

In case of providing internal air outlet slots 29, and flow into receiving space 31 of receiving means 5 from below is not desired, the receiving means may also be designed, as illustrated in FIG. 6c, namely with a bottom-side cover plate 55. The plate is preferably made from the same material and as one piece with receiving means 5, and prevents flowing into receiving space 31. In this case, cover plate 55 also forms the stop member that supports containers 34, 45 inserted into insertion slots 31, 32 in the desired position.

Only for the sake of completeness, it should be mentioned, that FIG. 6a represents a section along line A-A of FIG. 6b, while FIGS. 6b and 6c show different alternative embodiments of receiving means 5 in the direction of the arrow B of FIG. 6a. Of course, these embodiments shown in FIG. 6 may be transferred on any embodiments of receiving means of this invention idea.

As can best be seen in FIGS. 1e and 1h, in the region of connecting area 4 or docking region 22, covered by receiving means 5, a light emitting diode 56 is arranged. The diode, for example, can display the operating state (ON/OFF) of device 1 or of fan assembly 9. When the receiving means is made, for example, of transparent plastic and/or glass material, light emitting diode 56 can provide a beneficial light effect, for example, by illumination of the receiving means 5 or by illumination of the receiving space 31 or by illumination of the containers 34, 35.

Figure 2:
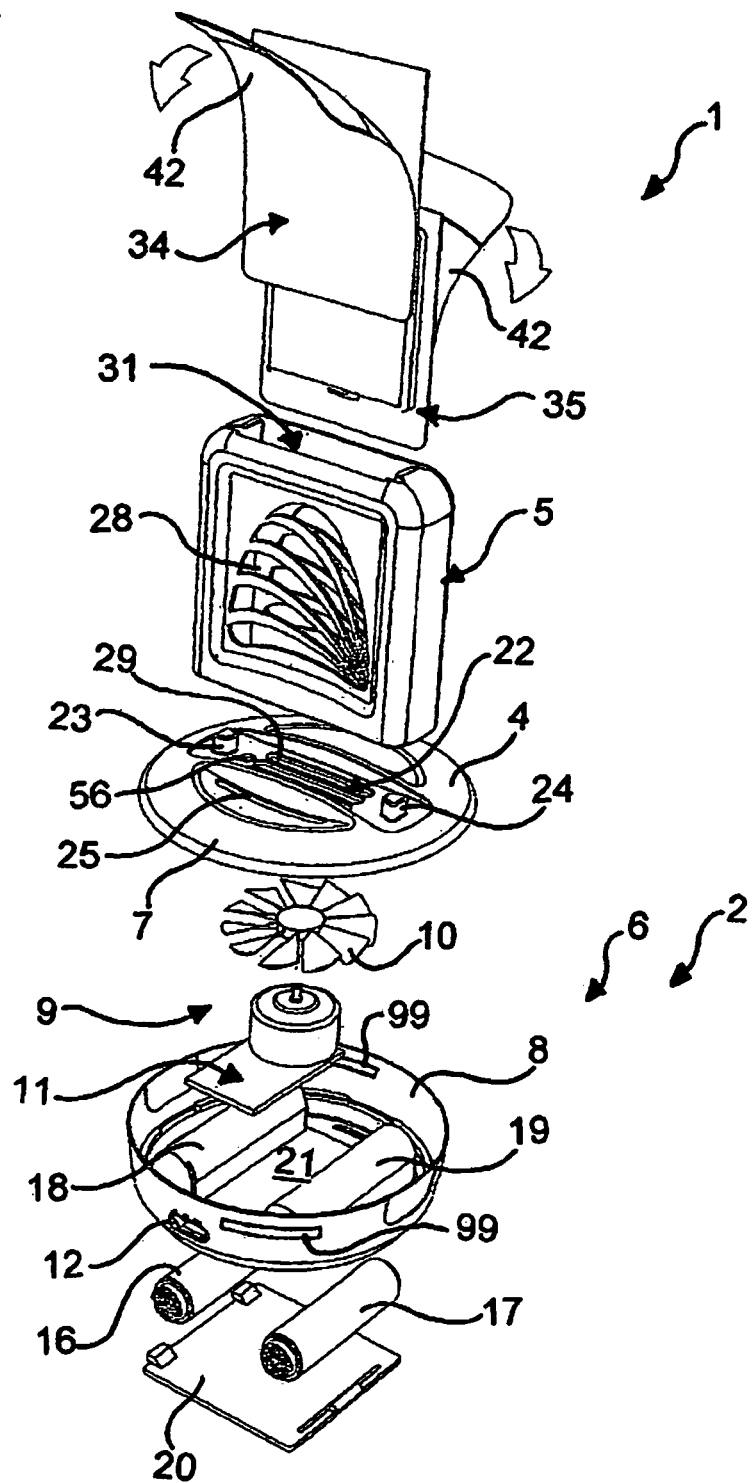

FIG. 2 shows an alternative embodiment which differs from that of FIG. 1 in that receiving means 5 has a different pattern of lateral air inlet slots 27, 28. Furthermore, in contrast to the embodiment according to FIG. 1, housing bottom 8 is designed tub or bowl-shaped, while housing top 7 is designed plate or disc-shaped, and the geometry of housing parts 7, 8 is inverted compared to the embodiment of FIG. 1. Housing side air inlet slots 99 in the region of the side wall of housing bottom 8 are only shown in a rather exemplary manner and schematically. Otherwise, the structure corresponds to FIG. 1, so that in this regard it is referred to earlier embodiments to avoid unnecessary repetitions, which is particularly true for the functionality of the device.

Figure 3:
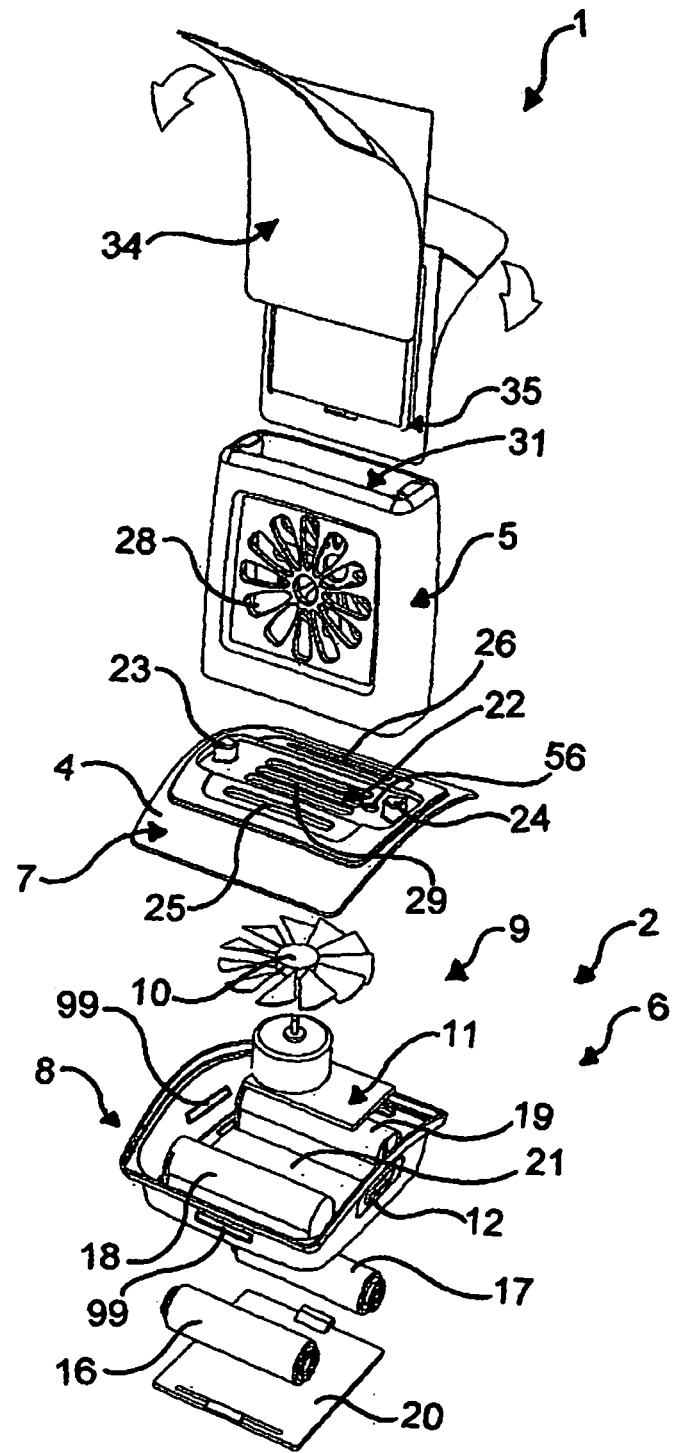
Figure 4A:
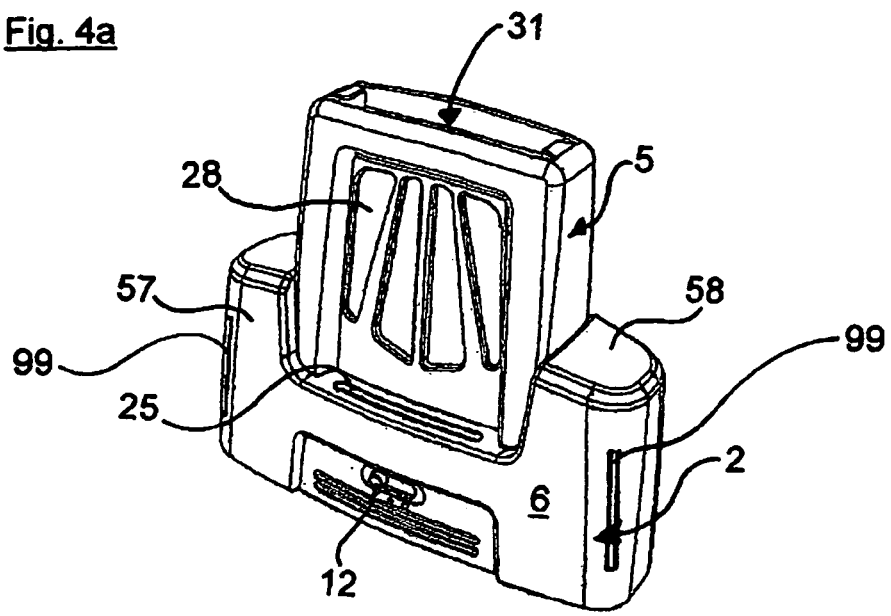
Figure 4B:
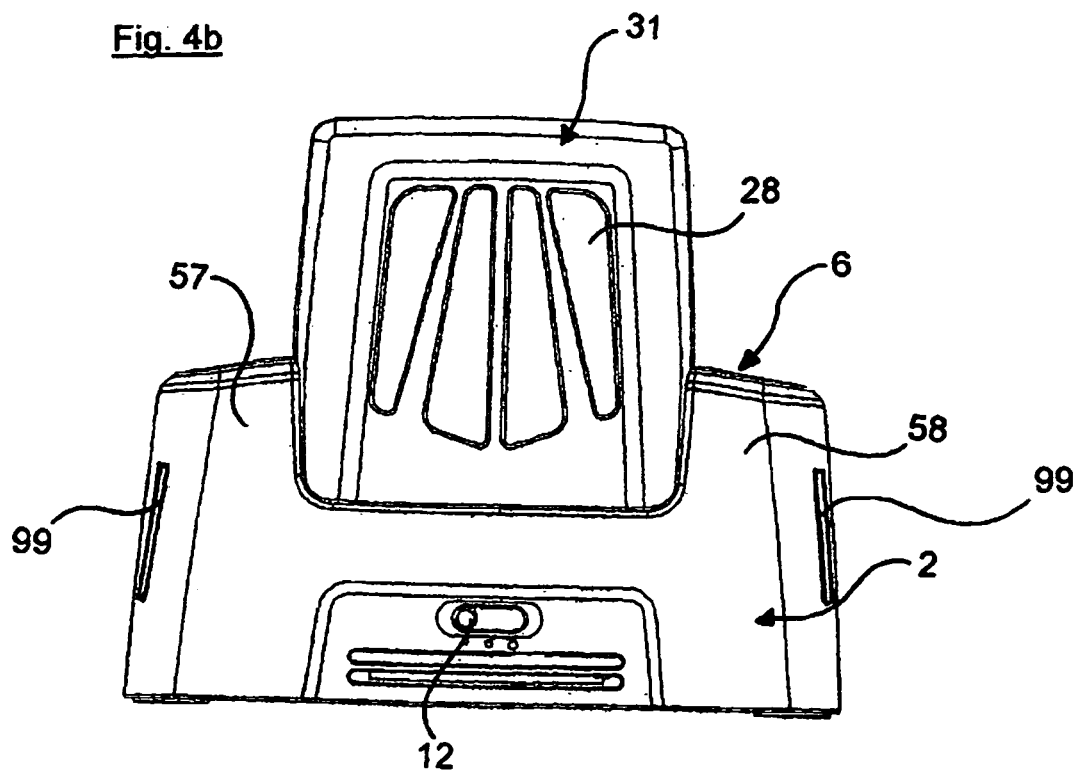
Figure 4D:
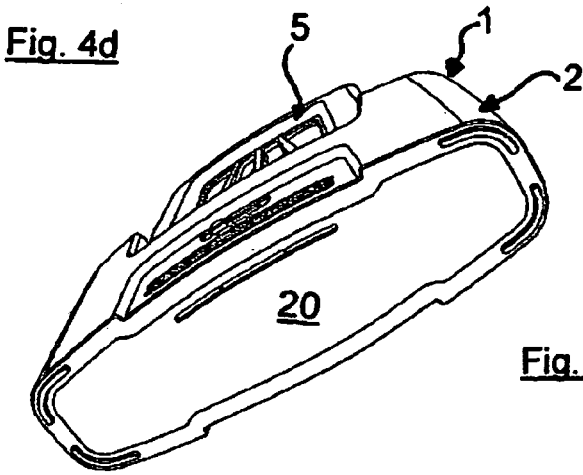
Figure 4E:
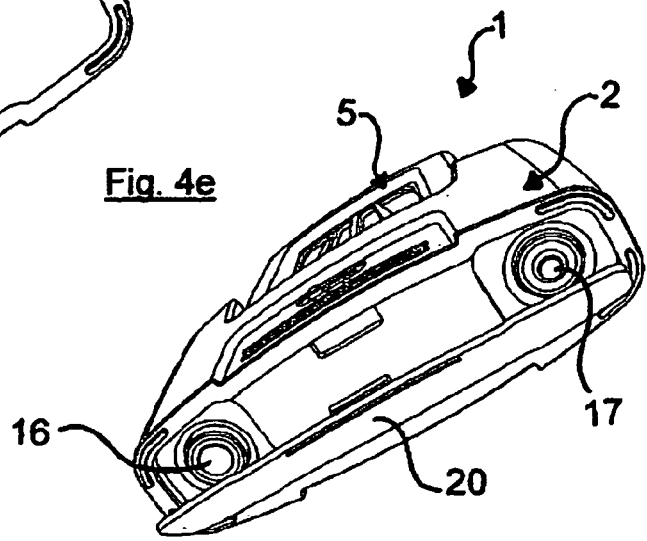
Figure 4F:
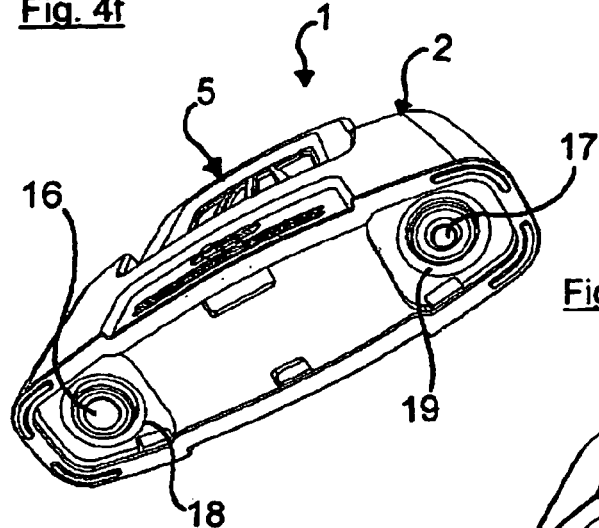
Figure 4G:
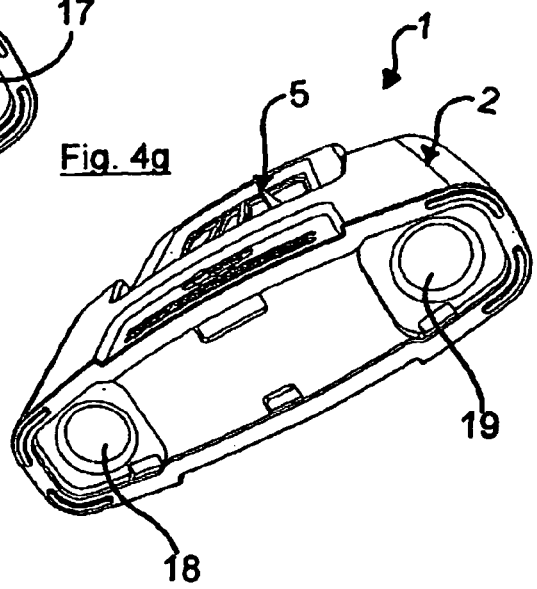

The same applies essentially to the embodiment variant according to FIG. 3, wherein lateral inlet slots 27, 28 of receiving means 5 form a sort of floral pattern. In further contrast to the embodiment according to FIG. 1 and according to FIG. 2, docking station 2 is formed with a vaulted, convex housing top 7, which can be connected to a tub-shaped housing bottom 8. In other respects the structure and functionality corresponds to that described in conjunction with FIG. 1.

Finally, in FIG. 4 a further alternative embodiment is illustrated, which differs from FIG. 1, in particular, by a different design of docking station 2. Docking station 2 does not have, as with the previous embodiments of FIGS. 1 to 3, horizontally mounted batteries or receiving compartments. Rather, relative to the operating or mounting position shown in FIGS. 4a and 4b, vertical receiving compartments 18, 19. Batteries 16, 17 are received correspondingly standing or vertically. Here again, as is particularly apparent from FIG. 4c, a mounting space 21 is arranged in the region between compartments 18, 19 for batteries 16, 17, in which fan assembly 9 is mounted and received (again optionally with additional electronic components and parts, such as regulating means 11). Receiving compartments 18, 19 are part of housing bottom 8, on which housing top 7 is placed. Housing top 7 has a U-shaped outer contour, with left and right sided U-legs 57, 58, in which receiving compartments 18, 19 are received. Connecting surface 4 for receiving means 5, and thus docking region 22 are arranged deeper and lower compared to the free ends of U-leg ends. In this case, the mounted or docked state of the receiving means 5, shown in FIG. 4a and in FIG. 4b, the two U-legs 57, 58 encompass and support substantially form-fittingly receiving means 5 at the opposing narrow sides. Of course, an additional fixing of receiving means 5 by means of latching projections 23, 24 can take place. Only latching projection 23 is shown in and is apparent from FIG. 4c. In other respects, the design and functionality corresponds to those of FIG. 1.

Housing side air inlet slots 99 are indicated only in an exemplary fashion and only schematically and are, for example, in the region of U-legs 57, 58.

Only for the sake of completeness, FIGS. 4d to 4g show bottom variant views for contact surface 3 and lid 20 latchably mounted there. The removal of lid 20 and the arrangement or configuration of batteries 16, 17 in conjunction with receiving compartments 18, 19 are shown in more detail.

While a preferred embodiment of the invention has been described using specific terms, such description is for illustrative purposes only, and it is to be understood that changes and variations may be made without department from the spirit or scope of the following claims.

I claim:

1. A device for dispensing volatile substances comprising;
a docking station;
a substance storage medium having a substance to be dispensed;
a receiver housing carried by said docking station for receiving said storage medium in a docked operating position on said docking station;
an air flow assembly housed below said storage medium for producing an air flow, wherein the air flow is directed toward said storage medium and the rate of dispensation of said substance into the environment is increased;
a station air inlet opening included in said docking station for receiving ambient air and a station air outlet included for the delivery of air to said receiver;
an air inlet opening included in said receiver housing for receiving said air from said station outlet opening for delivery to said storage medium; and
a receiving space in which said storage medium is retained in said receiving housing in flow communication with said docking station;
a membrane medium included in said storage medium carrying said substance to be volatilized, and said air flow being directed toward and around the membrane medium during operation so that the substance is volatized and dispensed into the environment;
a receptacle included in the storage medium said substance to be volatilized and dispensed being received in said receptacle;
said substance being one of a liquid and a gel and said membrane medium forming a wall of said receptacle in which said substance is received;
said receiving housing including an access opening through which said storage medium membrane is inserted;
said receiving space of the receiving housing including an insertion slot with spaced opposing guide grooves in which the storage medium engages with side edges for retention in an operation position;
said receiver housing in the docked operation position together with said storage medium carried thereon projects as a tower from the docking station which forms a base; and said station outlet opening and storage medium are arranged so that an air flow flows along and around a defined flow area of said storage medium prior to dispensing.

2. The device according to claim 1, wherein said docking station is designed as a separate device having an attachment area where said receiving housing attaches with said docking station.

3. The device according to claim 1 wherein said receiving housing has an outer wall section in which said receiver air inlet opening is formed, and said docking station includes a lateral air outlet opening whereby the air flow flowing through the lateral air outlet opening enters the receiver air inlet opening from the outside of the receiving housing.

4. The device according to claim 1, by further including a plurality of station air outlet openings arranged in the docking section around the receiving means, a side wall area of said receiving means having side receiver air inlet openings, arranged so that air flows exiting from the station side air outlet openings flow toward the air inlet openings along defined flow paths.

5. The device according to claim 1, wherein the receiving housing includes a second receiver air inlet opening, and said docking station includes a second air outlet, and said receiving housing covering the station second air outlet opening so that an air flow flows into the interior of receiving housing into a receiving space of the receiving housing.

6. The device according to claim 5, wherein the second receiver air inlet opening is formed so that the air flow flows around the storage medium from below along a defined pathway, and side air channels formed within the receiving housing includes said defined pathway which leads to the receiving space.

7. The device according to claim 1, further including an access opening formed in said receiver housing leading to the receiving space so that the storage medium can be inserted into the receiving space and disposed adjacent the lateral receiver air inlet opening enabling the air flow to flow into the receiving space.

8. The device according to claim 1, including a membrane included in the storage medium facing the receiver air inlet opening in such a way that the air flow flowing into the receiving means impinges upon the membrane.

9. The device according to claim 8, wherein the membrane is sealed with a detachable cover.

10. The device according to claim 9, wherein the membrane of the storage medium includes one of the two large side areas of the receptacle.

11. The device according to claim 1, wherein the receiving space includes a plurality of storage medium insertion slots spaced from one another transversely to the membrane insertion direction.

12. The device according to claim 1, including a regulating means to regulate said air flow assembly as a function of defined operating parameters such as the velocity of the air flow delivered to the storage medium, and the regulating means includes a processor storage in which different preprogrammed modes of operation and operating cycles are stored.

13. The device according to claim 1, including a light emitting device, having a display indicator indicating the operating state and operating mode, and one of the docking station, storage medium, and receiving housing can be illuminated.

14. A device for dispensing volatile substances comprising:
a docking station;
a substance storage medium carried by said docking station having a substance to be dispensed;
an air flow assembly housed below said storage medium for producing an air flow directed toward said storage medium to increase the rate of dispensation of said substance into the environment;
an air inlet included in said docking station for receiving ambient air and an air outlet included in said docking station for the delivery of air to said storage medium;
a receptacle included in the storage medium containing said substance to be volatized and dispensed;
a membrane medium carried by said receptacle and said air flow being directed toward and around the membrane medium during operation so that the substance is volatized and dispensed into the environment;
a retainer for storage medium for retaining said storage medium in an upright operating position.

15. The device of claim 14 including a receiver housing carried by said docking station for receiving said storage medium in said docked operating position on said docking station.

16. The device of claim 15 including a receiving space in which said storage medium is retained in said receiving housing in flow communication with said docking station.

17. The device of claim 14 wherein said docking station includes an outlet opening and said receiver housing includes an inlet so that a defined air flow flows along and around a defined flow area of said storage medium prior to dispensing.

18. The device of claim 14 wherein said retainer includes a receiver housing carried by said docking station, an access opening formed in said receiver housing leading to the receiving space so that the storage medium can be inserted into the receiving space and disposed adjacent the lateral receiver air inlet opening enabling the air flow to flow into the receiving space.

19. The device according to claim 18 wherein said membrane faces the air inlet in such a way that the air flow flowing into the receiving housing impinges upon the membrane.

20. The device according to claim 18 wherein said retainer includes releasable engaging members which engage said storage medium for retention in said receiving space.

21. A device for dispensing volatile substances comprising a docking station, a substance storage medium having a substance to be dispensed, a receiver housing carried by said docking station for retaining said storage medium in a docked operating position on said docking station, an air flow assembly housed below said storage medium for producing an air flow directed toward said storage medium increasing the rate of dispensation of said substance into the environment, a station air inlet included in said docking station for receiving ambient air and a station air outlet included for the delivery of air to said receiver housing, a receiver air inlet included in said receiver housing for receiving air from said station air outlet for delivery to said storage medium; and a receiving space in said receiver housing for retaining said storage medium in flow communication with said docking station, wherein said device comprises:
a membrane medium included in said storage medium in through which said substance is dispersed;
said air flow being directed toward and around the membrane medium during operation so that the substance is volatized and dispensed into the environment;
a receptacle included in the storage medium, said substance to be volatilized and dispensed being contained in said receptacle;

said substance being one of a liquid and a gel and said membrane medium forming a wall of said receptacle in which said substance is received;

an access opening formed in said receiving housing through which said storage medium is inserted;

opposed insertion guide elements carried within said receiving space of the receiving housing receiving and engaging said storage medium for retention in said operation position;

said station air outlet and storage medium being arranged so that said air flow flows along and around said defined flow area of said storage medium prior to dispensing.

22. The device according to claim 21, wherein the docking station is designed as a separate device having an attachment area where said receiving housing and said docking station are attached together.

23. The device of claim 21 wherein the receiving housing has an outer wall section in which said air inlet is formed whereby the air flow from the station air outlet enters the air inlet from the outside of the receiving housing.

24. The device of claim 21 wherein the receiving housing includes a second air inlet, said docking station includes a second air outlet, and said receiving housing covering the second air outlet of said docking station so that an air flow flows into the interior of said receiving space of the receiving housing.

25. The device according to claim 24, wherein the second air inlet of the receiver housing is formed so that the air flow flows around the storage medium from below along a defined pathway, and including side air channels formed in the receiving housing providing said defined pathway which leads to the receiving space.

26. The device of claim 21 including an access opening formed in said receiver housing leading to the receiving space so that the storage medium can be inserted into the receiving space and located adjacent the air inlet opening enabling the air flow to enter the receiving space.

27. The device of claim 22 including a receptacle containing said substance said membrane generally coextending with said substance in said receptacle.

28. A device for dispensing volatile substances comprising:

a docking station;

a substance storage medium carried by said docking station having a substance to be dispensed;

an air flow assembly housed below said storage medium for producing an air flow directed toward said storage medium to increase the rate of dispensation of said substance into the environment;

an air inlet included in said docking station for receiving ambient air and an air outlet included in said docking station for the delivery of air to said storage medium;

a receptacle included in the storage medium containing said substance to be volatized and dispensed;

a membrane medium carried by said receptacle adjacent through which said substance is dispersed, and said air flow being directed toward and around the membrane medium during operation so that the substance is volatized and dispensed into the environment.

29. The device of claim 28 including a retainer for holding said storage medium in an upright operating position above said docking station.

30. The device of claim 29 wherein said retainer includes a receiver housing carried by said docking station for receiving and holding said storage medium in said upright operating position on said docking station.

31. The device of claim 30 including a receiving space of said housing in which said storage medium is retained in flow communication with said docking station.

32. The device of claim 31 wherein said receiver housing includes an air inlet so that said air flow from said station outlet flows along and around a defined flow area of said storage medium prior to dispensing.

33. The device of claim 28 wherein said retainer includes a receiver housing carried by said docking station, an access opening formed in said receiver housing leading to an interior receiving space so that the storage medium can be inserted into the receiving space and located adjacent the air inlet of said receiver housing enabling the air flow to flow into the receiving space.

34. The device according to claim 33 wherein said membrane faces the air inlet in such a way that the air flow flowing toward the receiving housing impinges upon the membrane.

35. The device according to claim 34 wherein said receiving housing includes releasable engaging members which engage said storage medium for retention in said interior receiving space.

* * * * *